US005665344A

United States Patent [19]
Pair et al.

[11] Patent Number: 5,665,344
[45] Date of Patent: Sep. 9, 1997

[54] VOLATILES OF JAPANESE HONEYSUCKLE FLOWERS AS ATTRACTANTS FOR ADULT LEPIDOPTERAN INSECTS

[75] Inventors: Sammy D. Pair, Atoka, Okla.; Robert J. Horvat, Athens, Ga.

[73] Assignee: The United States of America as represented by the Secretary of Agriculture, Washington, D.C.

[21] Appl. No.: 556,182

[22] Filed: Nov. 9, 1995

[51] Int. Cl.$^6$ .......................... A01N 35/06; A01N 35/02; A01N 31/02
[52] U.S. Cl. ........................ 424/84; 514/675; 514/690; 514/699; 514/739; 426/1
[58] Field of Search ........................ 424/84; 426/1; 514/675, 690, 699, 739

[56] References Cited

U.S. PATENT DOCUMENTS

| | | | |
|---|---|---|---|
| 3,474,176 | 10/1969 | Freeman | 514/690 |
| 4,045,489 | 8/1977 | Wiegers et al. | 568/348 |
| 4,137,196 | 1/1979 | Sakurai et al. | 512/2 |

OTHER PUBLICATIONS

Pair, S.D., "Japanese Honeysuckle (Caprifolicaeae): Newly Discovered Host of *Heliothis virescens* and *Helicoverpa zea* (Lepidoptera: Noctuidae)", *Environmental Entomology*, vol. 2, No. 4, Aug. 1994, pp. 906–911.

Pair, S.D., "Attractancy of Japanese honeysuckle flowers to economically important *Lepidoptera*", 1994 ESA Annual Meeting, Dec. 13–17–1994, (mailed out Nov./16/94), Dalla Texas.

Flath, Robert A., et al., "Volatile Components of *Acacia* sp Blossoms", *J. Agric. Food Chemical*, vol. 31, No. 6, 1983, pp. 1167–1170.

*Primary Examiner*—John Pak
*Attorney, Agent, or Firm*—M. Howard Silverstein; Randall E. Deck; John D. Fado

[57] ABSTRACT

Compositions of cis-jasmone were found to effectively attract adult Lepidoptera. The cis-jasmone may be used alone or in combination with one or more other volatiles of the Japanese honeysuckle flower, particularly linalool and/or phenylacetaldehyde. By attracting the adult Lepidoptera to attracticidal baits and/or field traps, the attractants are useful for the control and monitoring of these agricultural pests.

12 Claims, No Drawings

VOLATILES OF JAPANESE HONEYSUCKLE FLOWERS AS ATTRACTANTS FOR ADULT LEPIDOPTERAN INSECTS

BACKGROUND OF THE INVENTION

1. Field of the Invention

This invention relates to attractants for both male and female adult Lepidopteran insects, particularly the cabbage looper, soybean looper, tobacco budworm, tobacco hornworm, and tomato hornworm.

2. Description of the Prior Art

Insects of the order Lepidoptera encompass a large number of pests responsible for substantial crop losses, reduced crop quality, and high production costs worldwide. Presently, the available monitoring systems and attracticidal baits for the majority of these pests utilize sex pheromones that are attractive to only one sex, usually the nonproductive male.

Recently, flowers of the Japanese honeysuckle, *Lonicera japonica*, were recognized as important ovipositional hosts of two important species of Lepidoptera, the tobacco budworm, *Heliothis virescens*, and the corn earworm, *Helicoverpa zea* (Pair, 1994, Environ. Entomol., 23(4):906–911). The chemistry of various Lonicera species has been partially described in several previous reports. Wu and Fang (1981, Acta Chemica Sinica, 38:573–579) analyzed the essential oil from flowers of *L. japonica*, and reported that linalool and linalool oxide C were the major identified constituents, and that pinene, 1-hexene, cis-3-hexen-1-ol, α-terpineol, geraniol, benzyl alcohol, β-phenylethanol, carvacol, eugenol, and some substituted furans were present in lesser amounts. In studies of pheromones and volatile honeysuckle attractants for the honeysuckle aphid, Hedin et al. (1991, J. Agric. Food Chem., 39:1304–1306) analyzed hexane-extractable volatiles from leaves and flowers of Lonicera species. Methyl esters, two ketones, seven alcohols, and three terpenoids (Δ-carene, (E)-β-faresene, and (E,E)-farnesol) were identified in the plant samples.

SUMMARY OF THE INVENTION

We have discovered that volatiles from the flowers of the Japanese honeysuckle (*Lonicera japonica*) are effective attractants for a variety of agronomically important adult Lepidoptera. Even more surprising, we have found that cis-jasmone, used alone or in combination with other Japanese honeysuckle flower volatiles, particularly linalool and/or phenylacetaldehyde, is effective for attracting these insects. The volatiles may be optionally used in combination with other agents including one or more of Lepidopteran pheromones, feeding stimulants, or insect toxicants.

In accordance with this discovery, it is an object of the invention to provide new compositions for attracting adult Lepidoptera as an aid to insect control measures.

Another object of the invention is to provide a means for increasing the effectiveness of insect traps for monitoring or suppressing Lepidoptera populations.

Other objects and advantages of this invention will become obvious from the ensuing description.

DETAILED DESCRIPTION OF THE INVENTION

According to this invention, there is provided compositions for attracting adult Lepidoptera, which include cis-jasmone, a volatile of the Japanese honeysuckle flower. Although the cis-jasmone may be used as the sole attractant, in the preferred embodiment insect attraction is substantially increased when the compound is used in combination with one or more other volatiles of the Japanese honeysuckle flower, particularly linalool and/or phenylacetaldehyde.

The volatile constituents of the Japanese honeysuckle flower were described by Scholtzhauer et al. (Journal Agricultural and Food Chemistry, in press) at three stages of flower development: freshly opened, flowers opened 12 hours, and flowers opened 24 hours. Twenty-seven compounds were identified among these three stages, although the absolute amounts of many of the constituents and their relative concentrations varied considerably between each stage. The volatiles, identified included, in no particular order: cis-3-hexen-1-ol, phenylacetaldehyde, linalool oxide (I), linalool oxide (II), methyl benzoate, linalool, methylphenylacetate, α-terpineol, methylsalicylate, β-citronellol, trans-geraniol, 2,4-decadienal, indole, cis-3-hexenyl tiglate, cis-jasmone, β-bourbonene, β-caryophyllene, geranylacetone, germacrene D, germacrene B, α-farnesene, hexenyl benzoate, nerolidol, methyl jasmonate, benzylbenzoate, benzylsalicylate, and methyl palmitate. Between the stages examined, the relative concentration of cis-jasmone in the volatile mixture varied from a low of 1.1% of the volatiles by weight in the 12 hour flowers to a high of 3.6% in the fresh flowers, linalool varied from 2.6% of the volatiles in the 12 hour flowers to 38.8% in the fresh flowers, and phenylacetaldehyde varied from 1.4% of the volatiles in the 24 hour flowers to 3.9% in the 12 hour flowers. In accordance with this invention, any one or more of the above-identified volatile constituents may be used in combination with cis-jasmone as an insect attractant.

The cis-jasmone of this invention is readily available from commercial sources, and is currently used in perfumes. Linalool, phenylacetaldehyde, and other Japanese honeysuckle flower volatiles contemplated by the invention are also available from commercial sources.

The attractants encompassed herein are effective in attracting and controlling a variety of agronomically important insects of the order Lepidoptera. While the pests of particular importance for control include *Trichoplusia ni* (cabbage looper), *Pseudoplusia includens* (soybean looper), *Heliothis virescens* (tobacco budworm), and *Manduca* species, especially *M. quinquemaculata* (tomato hornworm), and *M. sexta* (tobacco hornworm), other insects are effectively attracted to the attractants as well. Without being limited thereto, the attractants of this invention may be used to attract and control Lepidoptera including:

Noctuidae:

*Trichoplusia ni* (cabbage looper),

*Pseudoplusia includens* (soybean looper),

*Agrotis ipsilon* (black cutworm),

*Caenurgina erechtea* (forage looper),

*Helicoverpa zea* (corn earworm),

*Heliothis virescens* (tobacco budworm),

*Spodoptera frugiperda* (fall armyworm),

*Spodoptera exigua* (beet armyworm),

*Spodoptera ornithogalli* (yellowstriped armyworm),

*Anagrapha falcifera* (celery looper), and

*Pseudaletia unipuncta* (armyworm),

*Anticarsia gemmatalis* (velvetbean caterpillar)

Plutellidae:

*Plutella xylostella* (diamondback moth),

Pyralidae:

*Achyra rantalis* (garden webworm),
*Desmia funeralis* (grape leaffolder),
*Diaphania hyalinata* (melonworm), and
*Diaphania nitidalis* (pickleworm), and
Sphingidae:
*Manduca quinquemaculata* (tomato hornworm),
*Manduca sexta* (tobacco hornworm),
*Eumorpha achemon* (achemon sphinx),
*Agrius cingulata* (sweetpotato hornworm), and
*Hyles lineata* (whitelined sphinx).

Furthermore, the attractant compositions of this invention are effective for attracting both sexes of adult Lepidoptera. In contrast to most commercially available baits or lures which attract only males, we have unexpectedly discovered that the subject compositions attract females as well as males. Since female moths are the reproductive sex capable of laying eggs, the capture of females could serve as a major tool in reducing succeeding populations. Moreover, it is envisioned that this ability to attract females may significantly contribute to the effective attraction of the compositions toward conspecific males as a result of their sexual response toward trapped females.

Suitable formulations of the attractants include cis-jasmone in crude or impure form, such as oil from the flowers of the Japanese honeysuckle, or in substantially pure form. However, as a practical matter, it is expected that substantially pure cis-jasmone will be formulated with an inert carrier, and optionally with other Japanese honeysuckle flower volatiles, particularly linalool and/or phenylacetaldehyde, for use as an insect attractant composition. The practitioner skilled in the art will recognize that the cis-jasmone and these other volatiles may be formulated in a single or separate compositions. Inert carriers suitable for use herein are well known in the art and include but are not limited to alcohols, ethers, glycols, ketones, esters, and solid carriers such as clays, cellulose, rubber, or synthetic polymers.

Optionally, the cis-jasmone composition may be further formulated with other insect attractants such as pheromones of the target insects or insect extracts containing pheromones, or with conventional feeding stimulants such as saccharides. Lepidopteran pheromones suitable for use herein are generally well-known in the art. Overviews of the pheromones for many insects, including many Lepidoptera, have been described, and include, for example, Mayer and McLaughlin (Handbook of Insect Pheromones and Sex Attractants, CRC Press, Boca Raton, Fla., 1991) and Tamaki [Sex Pheromones, In Comprehensive Insect Physiology Biochemistry and Pharmacology, Vol. 9 Behavior, Kerkut and Gilbert (Ed.), Pergamon Press, New York, pp. 145–179].

The amount of cis-jasmone is selected to provide an effective attraction of the insects. The effective amount is defined herein as that quantity of attractant that attracts the target insects to the location of a bait at a rate significantly higher than the attraction to a nonbaited location (i.e. negative control). Effective concentrations of the cis-jasmone in the composition may vary, although concentrations with respect to other Japanese honeysuckle flower volatiles which are greater than or equal to about 10%, particularly greater than about 20%, provide optimal insect attractancy and are preferred. Suitable amounts and concentrations may be readily determined by a practitioner skilled in the art, and will of course vary with the particular target insect, its population density, the size of the area to be treated, environmental conditions such as temperature, humidity and wind conditions, the type of vehicle or carrier.

When employed in combination with other volatiles or attractants, the ratio and absolute amounts of all active ingredients may also vary and are similarly selected to provide an effective attraction of the target insects to the composition.

The attractant compositions may be used in a number of ways, including monitoring or controlling insect populations. In one preferred embodiment, the compositions may be placed within in traps to monitor population changes. Precise monitoring will enable growers to reduce the number of insecticide applications when populations are low. In other preferred embodiments, the attractants may be used to control pest populations by employing large numbers of traps (trap-out strategy), or by combination with an effective amount of an insect toxicant or pesticide to kill adult Lepidoptera (as an attracticidal bait). Use in this manner should prove useful in suppressing target species before they can inflict damage to agronomically important crops. Suitable toxicants for use herein may be readily selected by the practitioner skilled in the art and include but are not limited to organophosphate, carbamate, nitroguanidine, and synthetic pyrethroid insecticidess.

In the practice of any of the above-described embodiments, an attractant is used as a trap bait or is otherwise applied to the locus of or in the vicinity of infestation in an amount effective to attract the target insect. As above, an effective amount is defined as that quantity of attractant that attracts the target insects to the location of a bait at a rate significantly higher than the attraction to a nonbaited location. Factors such as population density, precipitation, temperature, wind velocity, and release rate will influence the actual number of insects trapped.

It is envisioned that the attractants may be used in conjunction with any type of appropriate trap or attractant disseminator as known in the art. The attractant can be applied or disseminated using a variety of conventional techniques, such as in an exposed solution, impregnated into a wicking material or other substrate, or incorporated in a deodorant dispenser. Further, the components of the attractant may be combined in a single dispenser provided within a single trap, or provided separately in a plurality of dispensers, all within a single trap. The attractant can be applied to the device undiluted, or formulated in an inert carrier. Volatilization can be controlled or retarded by inclusion of an extender such as mineral oil. Mineral oil alone is relatively unattractive to the insects. Controlled, slow release over an extended period of time may also be effected by placement within vials covered with a permeable septum or cap, by encapsulation using conventional techniques, or absorption into a porous substrate.

The following examples are intended only to further illustrate the invention and are not intended to limit the scope of the invention, which is defined by the claims.

EXAMPLE 1

Initial tests were conducted under field conditions to examine the attraction of adult Lepidoptera toward a mixture of cis-jasmone with linalool and phenylacetaldehyde as compared with various other treatments. Field bioassays were conducted in mixed plantings of vegetable crops near Lane, Okla.

The treatments tested included a 1:1:1 mixture of cis-jasmone, linalool and phenylacetaldehyde (PJL), compositions of all fresh or 12 hour Japanese honeysuckle flower volatiles, a 1:1:1:1 mixture of benzyl alcohol, geraniol, linalool, and phenyl ethyl alcohol (BGLP), and negative controls. Compounds were purchased from commercial sources. Baits representing the complete Japanese honeysuckle volatile mixture were prepared based upon their ratio as identified by Scholtzhauer et al. (ibid), which is shown in Table 1. Individual baits were prepared by dispensing 125 μl of each composition on a single dental wick saturated with 1 ml of light mineral oil to reduce volatilization. With the exception of the complete Japanese honeysuckle volatile mixture, mixtures of two or more compounds were applied in a 1:1 ratio totalling 125 μl per bait. Controls consisted of dental rolls saturated with mineral oil only. The treatments were replicated four times.

Standard 75-50 cm wire-cone pheromone traps described by Hartstack (1981, Environmental Entomology, 10:908–914) were used in all experiments. Single dental roll baits were attached with spring clips to the trap crossbar just beneath the trap opening. Traps were monitored and baits were replaced daily except on weekends. Insects captured in traps were removed and transferred to the laboratory where they were identified, sexed, and recorded.

The results are shown in Table 2. Baits containing constituents from fresh and 12 hour Japanese honeysuckle flower and the cis-jasmone/linalool/phenylacetaldehyde mixture captured the greatest numbers of cabbage looper, soybean looper, and total noctuid females than the BGLP blend or the untreated control. Tomato and tobacco hornworm females were attracted more to 12 hour based baits and to the BGLP mixture.

EXAMPLE 2

Field bioassays were conducted to determine the attractancy of baits containing cis-jasmone (jas), linalool (lin), and phenylacetaldehyde (phen) individually and in all possible combinations. The various baits assayed are shown in Table 3. The bioassays were conducted in the same manner described in Example 1.

The results are shown in Table 3. The addition of jasmone to phenylacetaldehyde resulted in significantly greater captures of cabbage looper and overall total numbers of noctuid females than the individual compounds alone or of other combinations of the three materials. An exception was the soybean looper in that the response to the phenylacetaldehyde bait was not statistically different from the jasmone/phenylacetaldehyde combination.

EXAMPLE 3

The field bioassays of Example 2 were repeated. The results are shown in Table 4. Baits containing combinations of cis-jasmone and linalool were more attractive to cabbage looper, *Manduca* species, and total noctuid females than all other baits. However, mixtures of cis-jasmone and the tri-mixture of all three compounds were more attractive to soybean loopers than other baits. No significant differences were noted in the response of corn earworm females to any of the baits, however, more females were captured in traps baited with cis-jasmone alone and in combination.

In the field bioassays of Examples 1, 2 and 3, a total of 21 economically important Lepidopteran moth species representing 4 families were captured in traps baited with individual and blends of Japanese honeysuckle volatiles. These species are shown in Table 5. Cabbage looper, soybean looper, and various moths belonging to the family Sphingidae were among the most prominent species collected. However, due to the seasonality of most species and low population densities of some species, the numbers and diversity of species collected varied from test to test.

It is understood that the foregoing detailed description is given merely by way of illustration and that modifications and variations may be made therein without departing from the spirit and scope of the invention.

TABLE 1

Volatile Compounds Identified in *Lonicera Japonica* Flowers

| | | Yield (μg/kilo.) | |
|---|---|---|---|
| GC PEAK | Compound | Fresh | 12 Hr. |
| 1 | cis-3-Hexen-1-ol | 70 | tr[a] |
| 2 | Phenylacetaldehyde | 366 | 279 |
| 3 | Linalool oxide (I)[b] | 120 | tr |
| 4 | Linalool oxide (II)[b] | 49 | 365 |
| 5 | Methyl benzoate[c] | nd[c] | 39 |
| 6 | Linalool | 6854 | 186 |
| 7 | Methylphenylacetate | 42 | 74 |
| 8 | α-terpineol | 81 | nd |
| 9 | Methylsalicylate | nd | 66 |
| 10 | β-citronellol | tr | tr |
| 11 | trans-geraniol | 107 | 48 |
| 12 | 2,4-decadienal | tr | tr |
| 13 | Indole | 52 | tr |
| 14 | cis-3-Hexenyl tiglate | 640 | 108 |
| 15 | cis-jasmone | 602 | 80 |
| 16 | β-bourbonene | nd | 62 |
| 17 | β-caryophyllene | 49 | 47 |
| 18 | Geranylacetone | tr | 172 |
| 19 | Germacrene D | 4806 | 3876 |
| 20 | Germacrene B | 186 | 149 |
| 21 | α-farnesene | 2058 | 68 |
| 22 | Hexenyl benzoate | 72 | 561 |
| 23 | Nerolidol | 476 | tr |
| 24 | Methyl jasmonate | 42 | nd |
| 25 | Benzylbenzoate | 46 | 602 |
| 26 | Benzylsalicylate | tr | 65 |
| 27 | Methylpalmitate | 242 | 442 |
| | TOTAL | 16960 | 7289 |

[a]trace = <20 μg/kilo
[b]cis and trans isomers not distinguished
[c]nd = not detected

TABLE 2

Response of pest Lepidoptera to traps baited with volatiles associated with Japanese Honeysuckle flowers.

| | | Total captured/bait[a] | | | | |
|---|---|---|---|---|---|---|
| Species | Sex | 12 hr[b] | fresh[b] | bglp[c] | tri-mix[d] | check |
| Cabbage looper | M | 142bc | 176b | 84c | 255a | 7d |
| | F | 218b | 240b | 78c | 328a | 9c |
| Soybean looper | M | 454a | 399a | 128b | 378a | 18b |
| | F | 438a | 305a | 120b | 361a | 6b |
| Manduca spp. | M | 7b | 7b | 28a | 7b | 1b |
| | F | 9ab | 4bc | 16a | 5bc | 0c |
| Corn earworm | M | 1b | 4a | 0b | 0b | 0b |
| | F | 1 | 4 | 2 | 2 | 1 |
| Total Noctuidae | F | 658a | 551a | 200b | 696a | 16b |
| Total Sphingidae | F | 15a | 9ab | 17a | 9ab | 0b |

[a]Means in a row followed by the same letter are not significantly different (P ≥ 0.05); Waller Duncan k-ratio test (SAS 1989).
[b]Fresh and 12-hr. baits were composed of all volatiles in their actual percentages present in fresh and 12-hr.-old Japanese honeysuckle flowers.
[c]Bait containing benzyl alcohol, geraniol, linalool, and phenyl ethyl alcohol in a 1:1:1:1 ratio.
[d]Mixture of cis-jasmone, linalool, and phenylacetaldehyde in a 1:1:1 ratio.

TABLE 3

Response of pest Lepidoptera to traps baited with volatiles associated with Japanese Honeysuckle flowers.

| | | Total captured/bait[a,b,c] | | | | | | |
|---|---|---|---|---|---|---|---|---|
| Species | Sex | jas | lin | phen | jas + lin | phen + jas | phen + lin | tri-mix[d] |
| Cabbage | M | 110bc | 65c | 98bc | 138b | 241a | 65c | 93bc |
| looper | F | 115b | 51c | 73bc | 114b | 217a | 58c | 73bc |
| Soybean | M | 10cd | 3d | 98a | 52b | 134a | 24bcd | 47bc |
| looper | F | 4c | 3c | 56a | 25bc | 73a | 17bc | 28b |
| Corn | M | 1 | 1 | 1 | 0 | 3 | 1 | 0 |
| earworm | F | 1 | 0 | 2 | 0 | 1 | 0 | 0 |
| Total Noctuidae | F | 121bc | 55d | 144b | 142b | 300a | 78cd | 107bcd |

[a]Means in a row followed by the same letter are not significantly different (P > 0.05); Waller Duncan k-ratio test (SAS, 1989).
[b]Key to compounds: jas = jasmonate, lin = linalool, phen = phenylacetaldehyde.
[c]Baits containing a single chemical were dispensed at 125 μl/bait; baits containing two or more were dispensed in a 1:1 ratio totaling 125 μl.
[d]Bait containing cis-jasmone, linalool, and phenylacetaldehyde in a 1:1:1 ratio.

TABLE 4

Response of pest Lepidoptera to traps baited with volatiles associated with Japanese Honeysuckle flowers.

| | | Total captured/bait[a,b,c] | | | | | | |
|---|---|---|---|---|---|---|---|---|
| Species | Sex | jas | lin | phen | jas + lin | phen + jas | phen + lin | tri-mix[d] |
| Cabbage | M | 383bc | 305cd | 184de | 610a | 382bc | 327c | 506ab |
| looper | F | 341b | 281bc | 164c | 568a | 297bc | 272bc | 383b |
| Soybean | M | 52cd | 44cd | 103bc | 93b | 98ab | 77bc | 130a |
| looper | F | 41cd | 17d | 81cd | 55cd | 102a | 69bc | 88ab |
| Manduca | M | 13a | 17a | 0b | 29a | 15a | 14a | 21a |
| spp. | F | 10bc | 6cd | 1d | 19a | 9bc | 5cd | 16ab |
| Corn | M | 0 | 2 | 1 | 1 | 0 | 0 | 0 |
| earworm | F | 5 | 4 | 1 | 2 | 3 | 0 | 4 |
| Total Noctuidae | F | 390bcd | 307cde | 240de | 634a | 412bc | 355bcd | 497ab |

[a]Means in a row followed by the same letter are not different (P > 0.05); Waller Duncan k-ratio test (SAS, 1989).
[b]Key to compounds: jas = jasmonate, lin = linalool, phen = phenylacetaldehyde.
[c]Baits containing a single chemical were dispensed at 125 μl/bait; baits containing two or more were dispensed in a 1:1 ratio totaling 125 μl.
[d]Bait containing cis-jasmone, linalool, and phenylacetaldehyde in a 1:1:1 ratio.

TABLE 5

Economically important Lepidoptra attracted to Japanese Honeysuckle volatiles.

| Species | Common Name |
|---|---|
| NOCTUIDAE | |
| Agrotis ipsilon | Black Cutworm |
| Anagrapha falcifera | Celery Looper |
| Anticarsia gemmatalis | Velvetbean Caterpillar |
| Caenurgina erechtea | Forage Looper |
| Helicoverpa zea | Corn Earworm |
| Heliothis virescens | Tobacco Budworm |
| Spodoptera frugiperda | Fall Armyworm |
| Spodoptera exigua | Beet Armyworm |
| Spodoptera ornithogalli | Yellowstriped Armyworm |
| Trichoplusia ni | Cabbage Looper |
| Pseudoplusia includens | Soybean Looper |
| Pseudaletia unipuncta | Armyworm |
| PLUTELLIDAE | |
| Plutella xylostella | Diamondback Moth |
| PYRALIDAE | |
| Achyra rantalis | Garden Webworm |
| Desmia funeralis | Grape Leaffolder |
| Diaphania hyalinata | Melonworm |
| Diaphania nitidalis | Pickleworm |
| SPHINGIDAE | |
| Eumorpha achemon | Achemon Sphinx |
| Agrius cingulata | Sweetpotato Hornworm |

TABLE 5-continued

Economically important Lepidoptra attracted to Japanese Honeysuckle volatiles.

| Species | Common Name |
| --- | --- |
| *Hyles lineata* | Whitelined Sphinx |
| *Manduca quinquemaculata* | Tomato Hornworm |
| *Manduca sexta* | Tobacco Hornworm |

We claim:

1. A composition for attracting insects comprising an attractant component which comprises at least two volatiles of the Japanese honeysuckle flower, one of said volatiles comprising cis-jasmone, and further wherein the concentration of cis-jasmone in said attractant component is greater than or equal to about 10% by weight.

2. A composition as described in claim 1 wherein said volatiles comprising said attractant component further comprise one or both of linalool and phenylacetaldehyde.

3. A composition as described in claim 2 wherein the ratio of cis-jasmone to linalool and phenylacetaldehyde combined is greater than or equal to about 1:2.

4. A composition as described in claim 2 wherein said volatiles comprising said attractant component further both linalool and phenylacetaldehyde.

5. A composition as described in claim 1 wherein the concentration of cis-jasmone in said attractant component is greater than or equal to about 20% by weight.

6. A composition as described in claim 1 further comprising an inert carrier.

7. A composition as described in claim 1, further comprising an insect toxicant.

8. A composition as described in claim 1 further comprising an insect pheromone.

9. A composition as described in claim 8 wherein said insect pheromone is a Lepidopteran pheromone.

10. A composition as described in claim 1 further comprising a feeding stimulant.

11. A composition as described in claim 10 wherein said feeding stimulant comprises a saccharide.

12. A composition as described in claim 1 wherein said volatiles comprising said attractant component are present in an amount effective as an insect attractant.

* * * * *